US00PP26732P2

(12) United States Plant Patent
Zaiger et al.

(10) Patent No.: US PP26,732 P2
(45) Date of Patent: May 17, 2016

(54) INTERSPECIFIC TREE NAMED 'POLAR PRIDE'

(50) Latin Name: **Interspecific *Prunus* species**
Varietal Denomination: Polar Pride

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 48 days.

(21) Appl. No.: 14/121,880

(22) Filed: Oct. 31, 2014

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Anne Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Regular and productive bearer of large size fruit.
3. Fruit with a high degree of attractive red skin color.
4. Fruit with very good flavor and eating quality.
5. Fruit with firm, white flesh.
6. Fruit with good storage and handling quality.

1 Drawing Sheet

Botanical designation: Interspecific *Prunus* species.
Variety denomination: 'Polar Pride'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific and nectarine trees, which are known to us, and mentioned herein, 'Honey Diva' Nectarine (U.S. Plant Pat. No. 15,291), 'Dapple Fire' Interspecific (U.S. Plant Pat. No. 12,409) and our proprietary non-patented interspecific varieties '48LW224', '55LR604' and '181GE42'.

STATEMENT REGARDING FEDERALLY SPONSORED RESEARCH AND DEVELOPMENT

Not applicable.

ORIGIN OF THE VARIETY

The new and distinct variety of interspecific tree which consists of the following species; *Prunus persica* var. *nucipersica, Prunus salicina* and *Prunus persica*, was developed by us in our experimental orchard located near Modesto, Calif. from open pollinated seed collected from our proprietary non-patented interspecific seedling selection with the field identification number '48LW224'. The non-patented interspecific seed parent (48LW224) originated as an open pollinated seedling selection from our proprietary non-patented interspecific seedling selection '55LR604'. '55LR604' is a first generation seedling from the proprietary seedling selection '181GE42' (non-patented) crossed with 'Dapple Fire' Interspecific (U.S. Plant Pat. No. 12,409). A large group of these open pollinated seedlings were planted and maintained on their own root system, during which time we recognized the desirable tree and fruit characteristics of the present seedling and selected it in 2009 for additional asexual propagation and commercialization.

ASEXUAL REPRODUCTION OF THE VARIETY

In 2009 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree Nectarine×[(Plum×Plum-nectarine)×(Peach×Plum Peach)] is of large size, vigorous, upright growth and is a regular and productive bearer of large size fruit with a high degree of attractive red skin color. The fruit is further characterized by having very good flavor and eating quality with a good balance between acid and sugar. In comparison to its proprietary non-patented interspecific seed parent (48LW224) the fruit of the new variety is larger in size and is approximately 3 days later in maturity. In comparison to the commercial variety 'Honey Diva' Nectarine (U.S. Plant Pat. No. 15,291) the fruit of the new variety is larger in size and has white flesh compared to yellow flesh.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters the first growing season. Varies with cultural practices, soil type, fertility and climatic conditions.

*Form*.—Upright growth, usually pruned to vase shape.

*Branching habit*.—Upright, crotch angle approximately 25°, increases with heavy crop load.

*Productivity*.—Productive, thinning and spacing of fruit desirable for marketable size. Fruit set varies with climatic conditions during bloom time.

*Bearer*.—Regular, adequate fruit set 3 consecutive years. No alternate bearing observed.

*Fertility*.—Self fertile.

*Density*.—Medium dense, usually pruned to vase shape to increase amount of sunlight to center of tree to enhance fruit color, Brix and health of fruit wood.

*Hardiness*.—Hardy in all stone fruit growing areas of California. Tree grown in USDA Hardiness Zone 9. Winter chilling requirement approximately 1000 hours at or below 45° F.

Trunk:

*Size*.—Large. Average circumference of 68.6 cm at 20.3 cm above ground on a 5 year old tree.

*Stocky*.—Medium stocky.

*Texture*.—Medium shaggy, becomes rougher with age.

*Color*.—Varies from 5Y 5/2 to 5Y 4/2.

Branches:

*Size*.—Medium. Average circumference 15.2 cm at 1.2 meters above ground. Crotch angle approximately 25°, increases with heavy crop load.

*Surface texture*.—New growth relatively smooth. Mature growth medium rough, roughness increases with age.

*Lenticels*.—Average number 40 in a 25.8 sq cm section. Average length 4.0 mm. Average width 1.5 mm. Color varies from 7.5YR 5/10 to 10YR 5/10.

*Color*.—New growth varies from 2.5GY 6/8 to 5GY 6/8. Mature growth varies from 7.5YR 3/4 to 10YR 3/4, varies with age of growth.

Leaves:

*Size*.—Large. Average length 148.2 mm. Average width 44.1 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Small. Average length 9.3 mm. Average width 1.7 mm. Longitudinally grooved. Surface — glabrous. Color varies from 5GY 5/6 to 5GY 5/8.

*Glands*.—Type — reniform. Size — medium. Average length 1.3 mm. Average diameter 1.0 mm. Average number 3, varies from 1 to 4. Located primarily on base of leaf blade and upper portion of petiole. Color varies from 5GY 6/8 to 5GY 5/8.

*Stipules*.—Average number 2. Average length 10.8 mm. Edges — pectinate. Color varies from 5GY 6/8 to 5GY 5/8.

*Color*.—Upper surface varies from 5GY 4/6 to 7.5GY 3/6. Lower surface varies from 5GY 4/4 to 7.5GY 4/4. Midvein color varies from 2.5GY 7/4 to 5GY 8/2.

Flower buds:

*Size*.—Large. Average length 17.1 mm. Average diameter 8.9 mm.

*Hardiness*.—Hardy with respect to California winters.

*Form*.—Conical, becoming elongated just before opening.

*Pedicel*.—Average length 3.4 mm. Average width 1.7 mm. Color varies from 2.5GY 6/10 to 5GY 6/8. Surface — glabrous.

*Density*.—Medium.

*Color*.—Varies from 7.5RP 8/4 to 5RP 8/6.

Flowers:

*Blooming period*.—Date of First Bloom Feb. 23, 2014. Date of Petal Fall Mar. 5, 2014, varies slightly with climatic conditions.

*Size*.—Large, showy. Average height 20.7 mm. Average diameter 39.8 mm.

*Petals*.—Normally 5, alternately arranged to sepals. Size — large. Average length 19.7 mm. Average width 15.4 mm. Form — elliptical. Petal apex — rounded. Petal base — rounded to somewhat truncated. Arrangement — overlapping. Margin — sinuate. Color varies from 2.5RP 8/8 to 7.5RP 5/12. Both upper and lower surfaces glabrous.

*Sepals*.—Normally 5, alternately arranged to petals. Size — large. Average length 6.1 mm. Average width 5.8 mm. Shape — ovate, apex rounded. Margin — entire. Color — upper surface varies from 5R 2/6 to 5R 3/4. Lower surface varies from 7.5R 3/4 to 5GY 5/8. Upper surface glabrous, lower surface pubescent.

*Stamens*.—Average number per flower 51, varies from 49 to 53. Average filament length 15.1 mm. Filament color varies from N 9.5/ (white) to 7.5RP 4/12 as flower ages. Anther color varies from 5R 3/6 to 5Y 8/4. On average, the stamens are below the height of the flowers.

*Pollen*.—Self fertile. Color varies from 5Y 8/14 to 5Y 8/10.

*Pistil*.—Normally 1. Surface — glabrous. Average length 18.9 mm. Position of stigma an average of 1.0 mm above anthers. Color varies from 2.5GY 7/10 to 5GY 7/8.

*Fragrance*.—Slight.

*Color*.—Varies from 5RP 8/4 to 5RP 8/8.

*Pedicel*.—Average length 3.9 mm. Average width 1.7 mm. Color varies from 2.5GY 8/8 to 2.5GY 7/8. Surface — glabrous.

*Number flowers per flower bud*.—Normally one.

Fruit:

*Maturity when described*.—Firm ripe and ready for consumption.

*Date of first picking*.—Aug. 3, 2014.

*Date of last picking*.—Aug. 13, 2014, varies slightly with climatic conditions.

*Size*.—Large. Average diameter axially 72.4 mm. Average transversely in suture plane 79.1 mm. Average weight 241.1 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Retuse.

*Base*.—Retuse.

*Stem cavity*.—Rounded to slightly elongated in suture plane. Average depth 12.4 mm. Average diameter 7.1 mm.

Stem:

*Size*.—Small to medium. Average length 8.9 mm. Average diameter 4.1 mm.

*Color*.—Varies from 10Y 6/6 to 2.5GY 7/8.

Flesh:

*Ripens*.—Evenly.

*Texture*.—Firm, meaty, crisp.

*Fibers*.—Few, small, tender.

*Firmness*.—Firm, comparable to other commercial varieties.

*Aroma*.—Moderate.

*Amydgalin*.—Undetected.

*Eating quality*.—Very good.

*Flavor*.—Very good, good balance between acid and sugar.

*Juice*.—Heavy amount, enhances flavor.

*Brix*.—Average Brix 15.2°, varies slightly with amount of fruit per tree and climatic conditions.

*Color*.—Varies from 5R 4/12 to 10Y 9/2.

*Pit cavity*.—Average length 37.5 mm. Average width 28.4 mm. Average depth 12.4 mm. Color varies from 5R 2/2 to 5R 3/10.

Skin:

*Thickness*.—Medium.

*Surface*.—Smooth.

*Pubescence*.—Wanting.

*Tendency to crack*.—None.

*Color*.—Ground color varies from 5Y 8.5/4 to 5Y 9/4. Overspread with 5R 4/10 to 5R 3/10.

*Tenacity*.—Tenacious to flesh.

*Astringency*.—Undetected.

Stone:

*Type*.—Clingstone, strong adherence to flesh.

*Size*.—Large. Average length 36.5 mm. Average width 27.4 mm. Average thickness 22.7 mm.

*Form*.—Obovoid.

*Base*.—Flat.

*Apex*.—Rounded.

*Surface*.—Pitted throughout, pits vary from rounded to slightly elongated.

*Sides*.—Unequal, one side extending further from the suture plane.

*Ridges*.—A small ridge on each side of suture extending from base toward apex.

*Tendency to split*.—None.

*Color*.—Varies from 7.5R 3/12 to 5R 4/10 when dry.

Kernel:

*Size*.—Large. Average length 18.2 mm. Average width 12.4 mm. Average depth 4.5 mm.

*Form*.—Ovoid.

*Viability*.—Viable, complete embryo development.

*Skin color*.—Varies from 5Y 9/6 to 5Y 8.5/6.

Use:

*Dessert*.—Market — local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

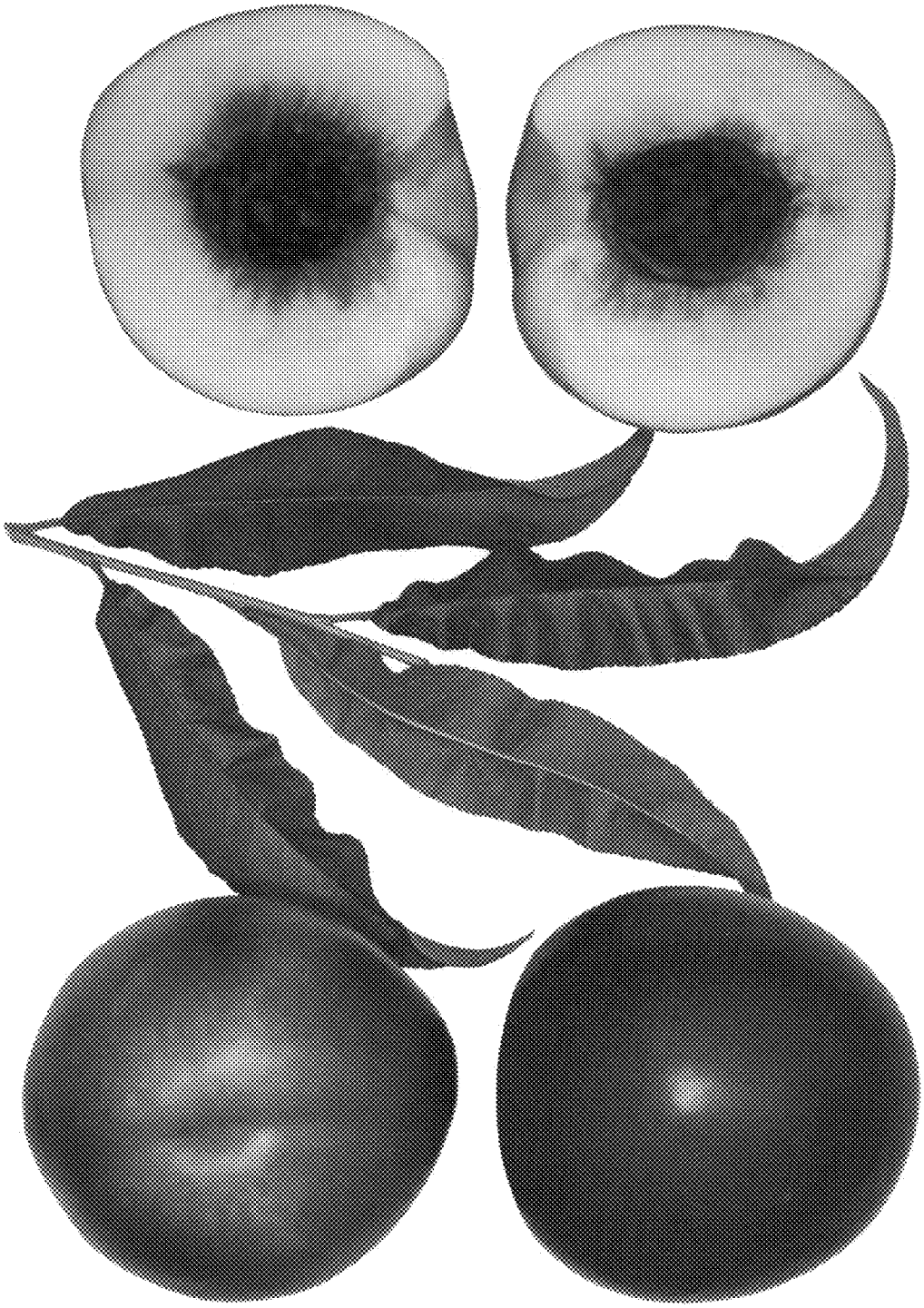

* * * * *